United States Patent
Lee et al.

(10) Patent No.: US 12,357,665 B2
(45) Date of Patent: Jul. 15, 2025

(54) PHARMACEUTICAL COMPOSITIONS AND USES THEREOF IN TREATING MUSCLE ATROPHY

(71) Applicant: Tzung-Yan Lee, New Taipei (TW)

(72) Inventors: Tzung-Yan Lee, New Taipei (TW); Hen-Hong Chang, Taichung (TW); Hsuan-Miao Liu, Hsinchu (TW); Wei-Han Chiang, Taipei (TW); Jheng-Huei Wang, Taoyuan (TW)

(73) Assignee: Tzung-Yan, New Taipei (TW)

( * ) Notice: Subject to any disclaimer, the term of this patent is extended or adjusted under 35 U.S.C. 154(b) by 309 days.

(21) Appl. No.: 17/921,142

(22) PCT Filed: Sep. 11, 2020

(86) PCT No.: PCT/CN2020/114666
§ 371 (c)(1),
(2) Date: Oct. 25, 2022

(87) PCT Pub. No.: WO2022/052017
PCT Pub. Date: Mar. 17, 2022

(65) Prior Publication Data
US 2023/0190846 A1    Jun. 22, 2023

(51) Int. Cl.
| | |
|---|---|
| *A61K 36/282* | (2006.01) |
| *A61K 31/12* | (2006.01) |
| *A61K 31/216* | (2006.01) |
| *A61K 31/235* | (2006.01) |
| *A61K 31/352* | (2006.01) |
| *A61K 31/353* | (2006.01) |
| *A61K 31/366* | (2006.01) |
| *A61K 31/704* | (2006.01) |
| *A61K 31/7048* | (2006.01) |
| *A61K 36/484* | (2006.01) |
| *A61K 36/533* | (2006.01) |
| *A61K 36/605* | (2006.01) |
| *A61K 36/81* | (2006.01) |
| *A61K 36/899* | (2006.01) |
| *A61K 36/9066* | (2006.01) |
| *A61P 21/00* | (2006.01) |

(52) U.S. Cl.
CPC ............ *A61K 36/282* (2013.01); *A61K 31/12* (2013.01); *A61K 31/216* (2013.01); *A61K 31/235* (2013.01); *A61K 31/352* (2013.01); *A61K 31/353* (2013.01); *A61K 31/366* (2013.01); *A61K 31/704* (2013.01); *A61K 31/7048* (2013.01); *A61K 36/484* (2013.01); *A61K 36/533* (2013.01); *A61K 36/605* (2013.01); *A61K 36/81* (2013.01); *A61K 36/899* (2013.01); *A61K 36/9066* (2013.01); *A61P 21/00* (2018.01); *A61K 2236/33* (2013.01)

(58) Field of Classification Search
None
See application file for complete search history.

(56) References Cited

FOREIGN PATENT DOCUMENTS

WO    WO 2017085190 A1 *  5/2017

* cited by examiner

*Primary Examiner* — Michael V Meller
(74) *Attorney, Agent, or Firm* — NZ Carr Law Office

(57) ABSTRACT

Disclosed herein are pharmaceutical compositions and uses thereof in treating muscle atrophy. The pharmaceutical composition comprises an ethanol extract of an herbal mixture consisting of *Artemisia argyi, Morus alba* L., *Leonurus japonicus* Houtt, *Capsicum annuum* L., *Lophatherum gracile* Brongn, *Curcuma longa*, and *Glycyrrhiza uralensis*; and a pharmaceutically acceptable excipient. The ethanol extract comprise 14 ingredients, including chlorogenic acid, leonurine, schaftoside, rutin, isochaftoside, isochlorogenic acid, 4, 5-dicaffeoylquinic acid, quercetin, apigenin, glycyrrhizic acid, bisdemethoxycurcumin, demethoxycurcumin, curcumin and artemisetin.

9 Claims, 9 Drawing Sheets

PHARMACEUTICAL COMPOSITIONS AND USES THEREOF IN TREATING MUSCLE ATROPHY

This application is a U.S. National Stage Filing under 35 U.S.C. 371 from International Patent Application Serial No. PCT/CN2020/114666, filed Sep. 11, 2020, and published on Mar. 17, 2022, the disclosure of which is incorporated by reference herein in its entirety.

BACKGROUND OF THE INVENTION

1. Field of the Invention

The present disclosure in general relates to the field of disease treatment. More particularly, the present disclosure relates to novel pharmaceutical compositions, and their uses in the treatment of muscle atrophy.

2. Description of Related Art

Adequate skeletal muscle plasticity plays an essential role in physical activity, and compromised muscle function can drastically affect the quality of life, morbidity and mortality of affected patients. Muscle atrophy, also known as muscle wasting disease, is a disease characterized in the loss of muscle tissue and progressive muscle weakness. Muscle atrophy may be caused by various factors, such as long periods of immobility, genetics, aging, malnutrition, medications, and/or various injuries or diseases that impact the musculoskeletal or nervous system. The symptoms of muscle atrophy vary with the cause and severity of muscle loss. In addition to reduced muscle mass, symptoms of muscle atrophy also include, difficulty or inability in performing physical tasks (e.g., standing, walking, climbing or balancing), curved spine (scoliosis), heart problems, swallowing problems, and even breathing problems.

Physical therapy (including specific stretches and exercise) provides some benefits to people having muscle atrophy via increasing muscle strength, improving circulation, reducing spasticity, and preventing immobility. Functional electrical stimulation (FES) is an alternative treatment for muscle atrophy. FES involves the use of electrical impulses to stimulate muscle contraction in affected muscles. However, these treatments merely slow down the progression of muscle loss without reversing or curing the disease. In severe cases of muscle atrophy, anabolic steroid (or anabolic-androgenic steroid (AAS); such as metandienone) may be administered to patients to alleviate the symptoms of muscle atrophy via enhancing their protein synthesis, glycogenesis, and muscle strength. Unfortunately, the use of anabolic steroid is limited by its side effects, including kidney problems or failure, liver damage (e.g., peliosis hepatis), heart problems (e.g., enlarged heart, high blood pressure, changes in blood cholesterol, artery damage, stroke, and heart attack), blood clots, cancer (e.g., testicular cancer or prostate cancer), infection (e.g., hepatitis or human immunodeficiency viral infection), hormone changes, and psychiatric problems (e.g., aggression, mania, and delusions).

In view of the foregoing, there exists in the related art a need for a new method and/or agent for treating muscle atrophy.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, the present disclosure is directed to novel pharmaceutical compositions, and their uses in the treatment of muscle atrophy.

The first aspect of the present disclosure is directed to a pharmaceutical composition comprising an ethanol extract of an herbal mixture consisting of *Artemisia argyi, Morus alba* L., *Leonurus japonicus* Houtt, *Capsicum annuum* L., *Lophatherum gracile* Brongn, *Curcuma longa*, and *Glycyrrhiza uralensis*; and a pharmaceutically acceptable excipient.

According to certain embodiments of the present disclosure, the ethanol extract is obtained via extracting *Artemisia argyi, Morus alba* L., *Leonurus japonicus* Houtt, *Capsicum annuum* L., *Lophatherum gracile* Brongn, *Curcuma longa*, and *Glycyrrhiza uralensis* by ethanol at about 30-100° C. for about 0.5-5 hours.

According to some preferred embodiments, the ethanol extract is obtained via extracting the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis* by 95% ethanol at about 50-80° C. for about 3-5 hours.

In some embodiments, during the extraction, the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis* are mixed at a weight ratio of about 4-6:4-6:4-6:2-3:2-3:1:1. According to specific examples, the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis* are mixed at a weight ratio of about 5:5:5:2.5:2.5:1:1.

According to certain embodiments, the thus-obtained ethanol extract comprises 14 herbal ingredients, including chlorogenic acid, leonurine, schaftoside, rutin, isoschaftoside, isochlorogenic acid, 4,5-dicaffeoylquinic acid, quercetin, apigenin, glycyrrhizic acid, bisdemethoxycurcumin, demethoxycurcumin, curcumin, and artemisetin. According to some working examples, the herbal ingredient-containing ethanol extract provides a potential means to treat muscle atrophy via regulating different molecules in atrophy pathogenic pathway and/or improving mitochondrial function.

The second aspect of the present disclosure thus pertains to a pharmaceutical composition comprising a mixture of chlorogenic acid, leonurine, schaftoside, rutin, isoschaftoside, isochlorogenic acid, 4,5-dicaffeoylquinic acid, quercetin, apigenin, glycyrrhizic acid, bisdemethoxycurcumin, demethoxycurcumin, curcumin, and artemisetin; and a pharmaceutically acceptable excipient.

According to some embodiments of the present disclosure, the mixture comprises 5-10 wt % of chlorogenic acid, 0.1-2 wt % of leonurine, 0.1-2 wt % of schaftoside, 5-10 wt % of rutin, 35-45 wt % of isoschaftoside, 20-30 wt % of isochlorogenic acid, 3-6 wt % of 4,5-dicaffeoylquinic acid, 0.1-0.5 wt % of quercetin, 1-3 wt % of apigenin, 1-3 wt % of glycyrrhizic acid, 1-3 wt % of bisdemethoxycurcumin, 1-3 wt % of demethoxycurcumin, 5-10 wt % of curcumin, and 0.1-0.5 wt % of artemisetin.

In certain preferred embodiments, the mixture comprises 7-8 wt % of chlorogenic acid, 0.5-1 wt % of leonurine, 0.5-1.5 wt % of schaftoside, 7-8 wt % of rutin, 38-42 wt % of isoschaftoside, 20-25 wt % of isochlorogenic acid, 4-5 wt % of 4,5-dicaffeoylquinic acid, 0.1-0.3 wt % of quercetin, 1-2 wt % of apigenin, 1-2 wt % of glycyrrhizic acid, 2-3 wt % of bisdemethoxycurcumin, 2-3 wt % of demethoxycurcumin, 5-7 wt % of curcumin, and 0.1-0.3 wt % of artemisetin.

Also disclosed herein is a method of treating muscle atrophy in a subject by use of the present pharmaceutical composition. The method comprises administering to the subject an effective amount of the pharmaceutical composition in accordance with any aspect or embodiment of the present disclosure.

According to some embodiments of the present disclosure, the pharmaceutical composition is orally or topically administered to the subject. In preferred embodiments, the pharmaceutical composition is administered to the subject daily for at least 7 days; more preferably, at least 14 days. In one specific example, the pharmaceutical composition is administered to the subject daily for 14 days.

The subject treatable with the present pharmaceutical composition and/or method is a mammal; preferably, a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 4A: protein levels of phosphorylated insulin-like growth factor-1 receptor (pIGF1R), IGF1R, phosphorylated insulin receptor substrate 1 (pIRS1), IRS1, phosphorylated phosphoinositide 3-kinase (pPI3K), PI3K, phosphorylated AKT (pAKT), AKT, phosphorylated mammalian target of rapamycin (pmTOR), mTOR, phosphorylated ribosomal S6 kinase (pS6K), S6K, phosphorylated eukaryotic translation initiation factor 4E (eIF4E)-binding protein 1 (p4EBP1), p4EBP1, and β-actin; FIG. 4B: the expression ratios of pIGF1R to IGF1R, and pIRS1 to IRS1 (Panel (A)), the expression ratios of pPI3K to PI3K, and pAKT to AKT (Panel (B)), and the expression ratio of pmTOR to mTOR, pS6K to S6K, and p4EBP1 to 4EBP1 (Panel (C)); results were expressed as the mean±S.E.M. of five independent experiments, and statistical significance of differences between means was assessed using an unpaired Student's t-test; *$p<0.05$, the normal control group compared to the sucrose group; #$p<0.05$, the sucrose group compared to the sucrose+ATG-125 group; ¥$P<0.05$, the sucrose group compared to the sucrose+4-OHT group;

DETAILED DESCRIPTION OF THE INVENTION

Figure 1:
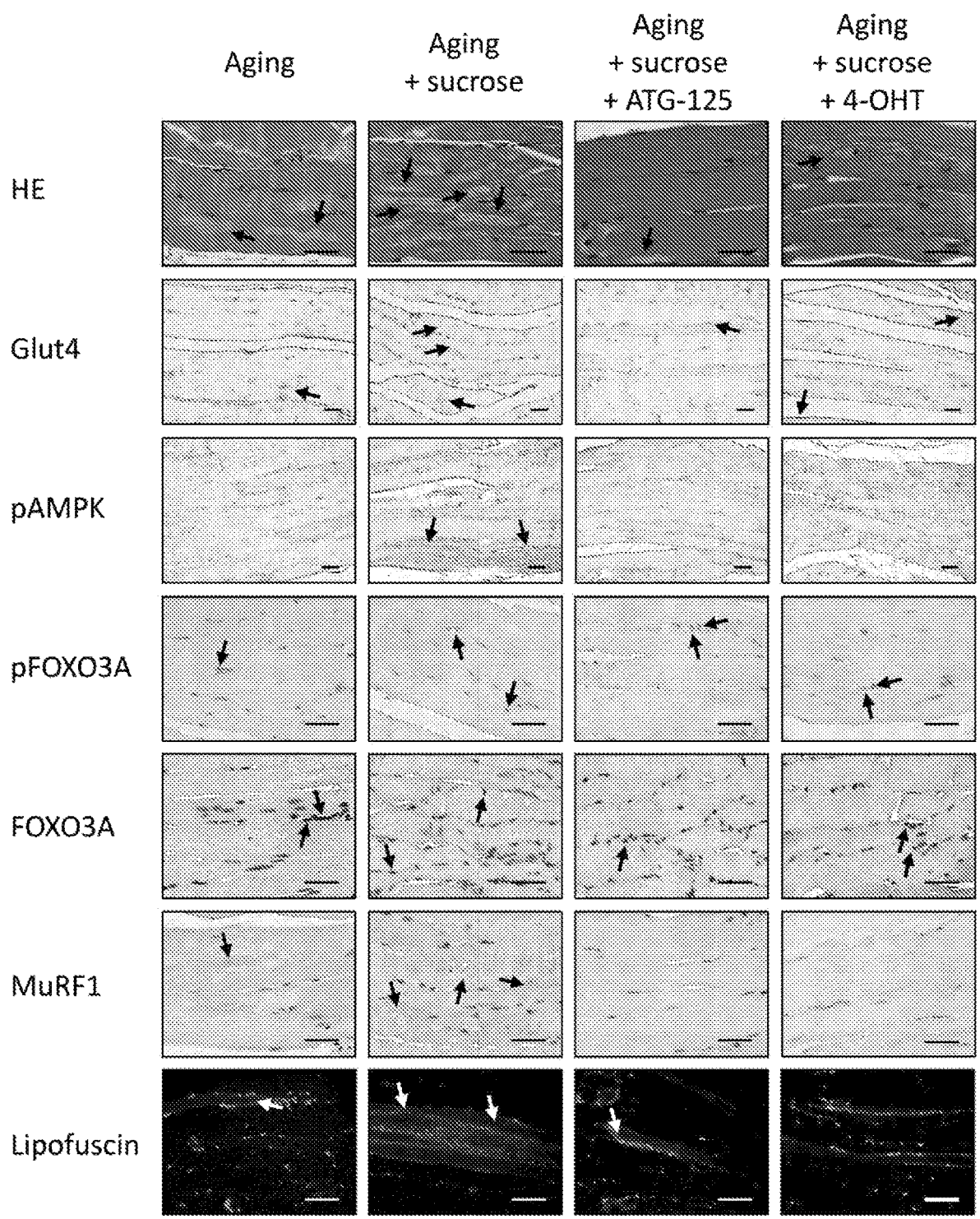
FIG. 1 are representative photographs of the muscle tissues of mice administered with specified treatments according to Example 1 of the present disclosure, in which the muscle tissues were stained by hematoxylin and eosin (H&E), and anti-glucose transporter type 4 (Glut4) antibody, anti-phosphorylated AMP-activated protein kinase (pAMPK) antibody, anti-phosphorylated forkhead box O3a (pFOXO3a) antibody, anti-FOXO3a antibody, anti-muscle RING-finger protein-1 (MURF1) antibody, or anti-lipofuscin antibody; the positive cells were marked by arrows; the visualization of lipofuscin's autofluorescence was detected at 450-490 nm; scale bar: 100 μm.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. DEFINITION

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "atrophy" as used herein means a decrease in the size and/or number of cells of a tissue (e.g., a muscle tissue) or organ after the tissue or organ has achieved its normal size. The term "muscle atrophy" as used herein refers to a loss of muscle mass and strength. Muscle atrophy may be a partial or complete wasting away of muscle(s), and may occur in any muscle of a subject, including skeletal muscle (e.g., biceps muscle, quadriceps muscle, gastrocnemius muscle, tibialis anterior muscle, forearm muscles, abdominal muscles, and paraspinal muscles) and non-skeletal muscle (e.g., diaphragm, and extraocular muscle).

As used herein, the term "extract" encompasses crude extracts as well as processed or refined extract. Specifically, crude extracts are prepared by a simple extraction in which selected plant ingredients are bought into contact with at least one extractant (i.e., extracting solvent). In some optional cases, the thus-obtained crude extracts are subjected to one or more separation and/or purification steps to obtain purified, processed or refined extracts. The plant extract may be in liquid form, such as a solution, concentrate, or distillate; or it may be in solid form in which the solvent is removed, such as in paste, granulate or powder form.

The term "weight percentage" (wt %) as used herein refers to the weight percentage of an ingredient (e.g., the chlorogenic acid, leonurine, schaftoside, rutin, isoschaftoside, isochlorogenic acid, 4,5-dicaffeoylquinic acid, quercetin, apigenin, glycyrrhizic acid, bisdemethoxycurcumin, demethoxycurcumin, curcumin, or artemisetin of the present pharmaceutical composition) in a mixture containing the ingredient. The weight percentage (wt %) is calculated as the weight of the ingredient divided by the total weight of the mixture expressed in percentage and/or decimal.

As used herein, the term "weight ratio" refers to the amounts of each component (e.g., the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis*) in a mixture (e.g., the herbal mixture of the present disclosure) as a ratio of the weight of each component.

As used herein, the term "treat," "treating" and "treatment" are interchangeable, and encompasses partially or completely preventing, ameliorating, mitigating and/or managing a symptom, a secondary disorder or a condition associated with muscle atrophy. The term "treating" as used herein refers to application or administration of the pharmaceutical composition of the present disclosure to a subject, who has a symptom, a secondary disorder or a condition associated with muscle atrophy, with the purpose to partially or completely prevent, alleviate, ameliorate, relieve, delay onset of, inhibit progression of, reduce severity of, and/or reduce incidence of one or more symptoms, secondary disorders or features associated with muscle atrophy. Symptoms, secondary disorders, and/or conditions associated with muscle atrophy include, but are not limited to, reduced muscle mass and/or strength, difficulty or inability in performing physical tasks (e.g., standing, walking, climbing or balancing), curved spine (scoliosis), heart problems, swallowing problems, and breathing problems. Treatment may be administered to a subject who exhibits only early signs of such symptoms, disorder, and/or condition for the purpose of decreasing the risk of developing the symptoms, secondary disorders, and/or conditions associated with muscle atrophy. Treatment is generally "effective" if one or more symptoms or clinical markers are reduced as that term is defined herein. Alternatively, a treatment is "effective" if the progression of a symptom, disorder or condition is reduced or halted.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the mixture of specified compounds, or the ethanol extract of the herbal mixture of the present pharmaceutical composition), such as molar concentration, mass concentration, volume concentration, molality, mole fraction, mass fraction and mixing ratio. Persons having ordinary skills could calculate the human equivalent dose (HED) for the medicament (such as the pharmaceutical composition of the present disclosure) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The terms "subject" and "patient" are used interchangeably herein, and are intended to mean an animal including the human species that is treatable by the pharmaceutical composition and/or method of the present invention. The term "subject" or "patient" intended to refer to both the male and female gender unless one gender is specifically indicated. Accordingly, the term "subject" or "patient" comprises any mammal, which may benefit from the pharmaceutical composition or the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the subject is a human.

II. DESCRIPTION OF THE INVENTION (i) Pharmaceutical Compositions

The subject invention aims at providing methods of treating muscle atrophy in a subject, as well as the pharmaceutical preparations or the dietary supplements for use in practicing the subject methods.

Accordingly, the first aspect of the present disclosure pertains to a pharmaceutical composition, which provides a potential means to treat a subject having or suspected of having muscle atrophy. The pharmaceutical composition comprises an extract of an herbal mixture consisting of *Artemisia argyi* (commonly known as "silvery wormwood" or "Chinese mugwort"), *Morus alba* L. (also known as "white mulberry"), *Leonurus japonicus* Houtt (also known as "Chinese motherwort"), *Capsicum annuum* L. (commonly known as "chili" or "pepper"), *Lophatherum gracile* Brongn, *Curcuma longa* (commonly known as "turmeric"), and *Glycyrrhiza uralensis* (also known as "Chinese liquorice"); and a pharmaceutically acceptable excipient.

According to some embodiments, *Artemisia argyi*, *Morus alba* L., *Leonurus japonicus* Houtt, *Capsicum annuum* L., *Lophatherum gracile* Brongn, *Curcuma longa*, and *Glycyrrhiza uralensis* are mixed and extracted by an appropriate solvent (e.g., water or ethanol) at suitable temperature for a period of time so as to obtain the present extract, which contains active ingredients, i.e., ingredients providing therapeutically beneficial effects on muscle atrophy.

Depending on desired purposes, the solvent for extracting said herbs (i.e., a combination of *Artemisia argyi*, *Morus alba* L., *Leonurus japonicus* Houtt, *Capsicum annuum* L., *Lophatherum gracile* Brongn, *Curcuma longa*, and *Glycyrrhiza uralensis*) may be a supercritical fluid (SFC; such as carbon dioxide, water, methane, ethane, propane, ethene, propene, methanol, ethanol, and acetone), water, $C_{1-4}$ alcohol (such as ethanol, 1-propanol, n-butanol, iso-butanol, and ter-butanol), acetone, ethyl acetate, n-hexane, or a combination thereof. According to some embodiments, said herbs are extracted by 75-100% (such as 75, 76, 77, 78, 79, 80, 81, 82, 83, 84, 85, 86, 87, 88, 89, 90, 91, 92, 93, 94, 95, 96, 97, 98, 99, or 100%) ethanol at a temperature of about 30-100° C. (such as 30, 35, 40, 45, 50, 55, 60, 65, 70, 75, 80, 85, 90, 95, or 100° C.) for a period of about 0.5-5 hours (such as 0.5, 0.6, 0.7, 0.8, 0.9, 1, 1.5, 2, 2.5, 3, 3.5, 4, 4.5, or 5 hours) thereby obtaining the extract of the present pharmaceutical composition.

According to certain examples, the extract of the present pharmaceutical composition is prepared via mixing the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis*, followed by extracting the mixed herbal parts or the herbal mixture by 95% ethanol at about 50-80° C. for about 3-5 hours. In one exemplary embodiment, the extract of the present pharmaceutical composition is prepared by extracting said herbal mixture or herbal parts (i.e., the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis*) by 95% ethanol at about 70° C. for about 4 hours.

According to certain embodiments of the present disclosure, said herbal parts are mixed at a weight ratio of about 4-6 (e.g., 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or 6):4-6 (e.g., 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or 6):4-6 (e.g., 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or 6):2-3 (e.g., 2, 2.1, 2.2, 2.3, 2.4, 2.5, 2.6, 2.7, 2.8, 2.9, or 3):2-3 (e.g., 2, 2.1, 2.2, 2.3, 2.4, 2.5, 2.6, 2.7, 2.8, 2.9, or 3):1:1. As could be appreciated, the person having ordinary skill in the art may adjust the ratio of said herbal parts in accordance with intended purposes. For example, said herbal parts may be mixed at a weight ratio of about 4:4:4:2:2:1:1. Alternatively, said herbal parts may be mixed at a weight ratio of about 4.5:5:6:2.5:2:1:1. Still alternatively, said herbal parts may be mixed at a weight ratio of about 5:5:5:2:3:1:1. According to some working examples of the present disclosure, said herbal parts are mixed at a weight ratio of about 5:5:5:2.5:2.5:1:1, and extracted by the solvent to produce a crude extract. The crude extract may subsequently be filtered, concentrated and/or lyophilized (i.e., freeze-dried) to produce a crude extract powder or paste. Alternatively, it may be subject to further purification, such as column chromatography or precipitation, to produce a refined extract.

According to some embodiments, the thus-obtained extract contains active ingredients useful in treating muscle atrophy; the active ingredients include, at least, chlorogenic acid, leonurine, schaftoside, rutin, isoschaftoside, isochlorogenic acid, 4,5-dicaffeoylquinic acid, quercetin, apigenin, glycyrrhizic acid, bisdemethoxycurcumin, demethoxycurcumin, curcumin, and artemisetin.

Thus, the second aspect of the present disclosure provides a pharmaceutical composition comprising a mixture of 14 active ingredients, and a pharmaceutically acceptable excipient, in which the 14 active ingredients including, (1) chlorogenic acid, which has a structure of

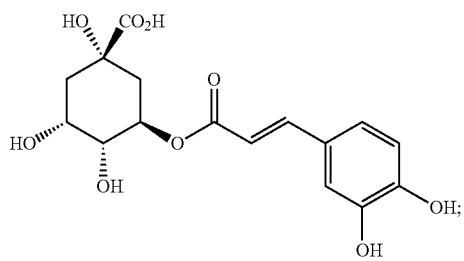 [SMILES: O=C(/C=C/c1ccc(O)c(O)c1)O[C@@H]1C[C@](O)(C(=O)O)C[C@@H](O)[C@H]1O]

(2) leonurine, which has a structure of

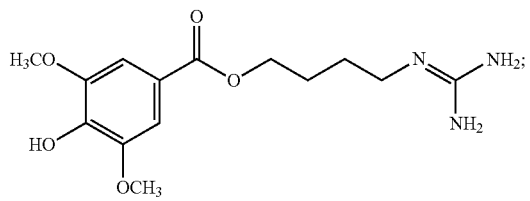 [SMILES: COc1cc(C(=O)OCCCCN=C(N)N)cc(OC)c1O]

(3) schaftoside, which has a structure of

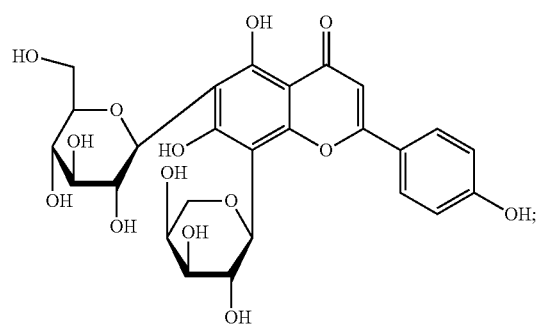

(4) rutin, which has a structure of

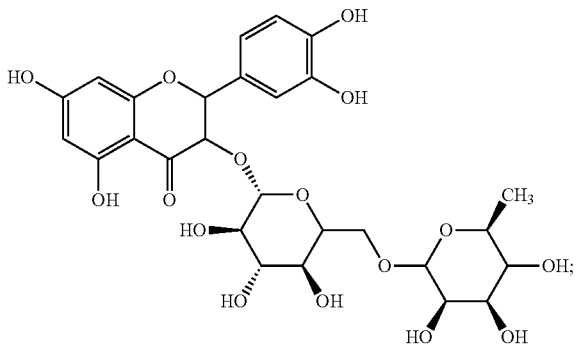 [SMILES: C[C@@H]1OC(OCC2O[C@@H](OC3C(=O)c4c(O)cc(O)cc4OC3c3ccc(O)c(O)c3)[C@H](O)[C@@H](O)[C@@H]2O)[C@H](O)[C@H](O)C1O]

(5) isoschaftoside, which has a structure of

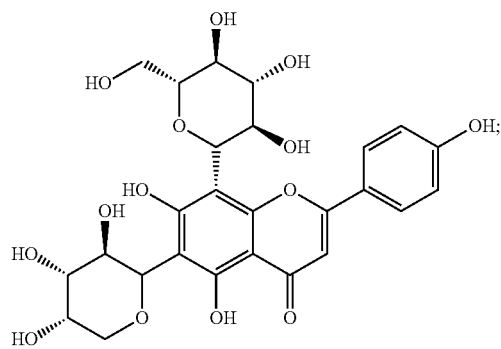

(6) isochlorogenic acid, which has a structure of

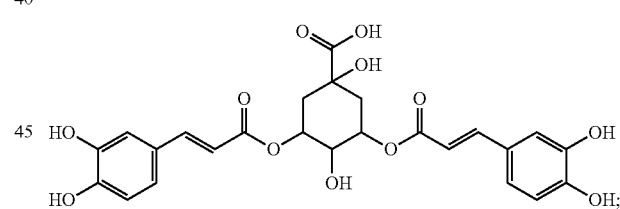

(7) 4,5-dicaffeoylquinic acid, which has a structure of

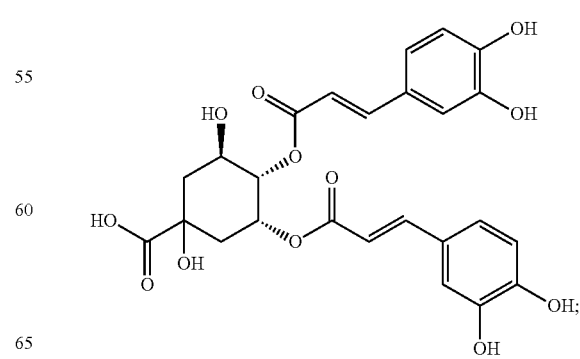

(8) quercetin, which has a structure of

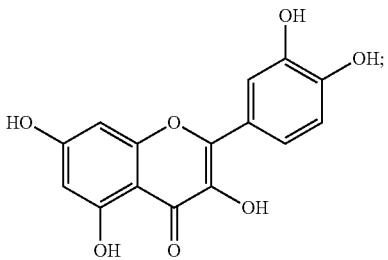 [SMILES: O=c1c(O)c(-c2ccc(O)c(O)c2)oc2cc(O)cc(O)c12]

(9) apigenin, which has a structure of

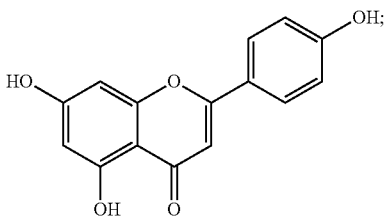 [SMILES: O=c1cc(-c2ccc(O)cc2)oc2cc(O)cc(O)c12]

(10) glycyrrhizic acid, which has a structure of

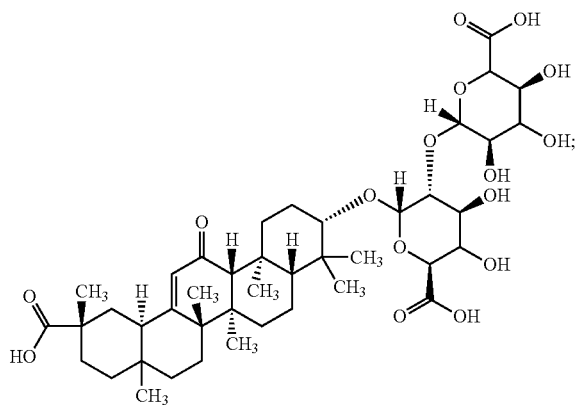

(11) bisdemethoxycurcumin, which has a structure of

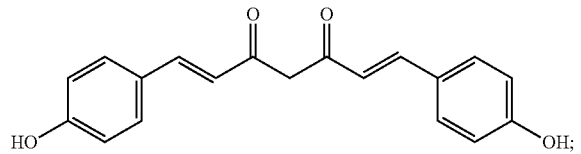 [SMILES: O=C(/C=C/c1ccc(O)cc1)CC(=O)/C=C/c1ccc(O)cc1]

(12) demethoxycurcumin, which has a structure of

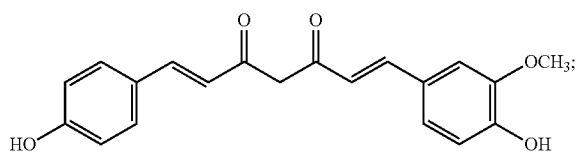 [SMILES: COc1cc(/C=C/C(=O)CC(=O)/C=C/c2ccc(O)cc2)ccc1O]

(13) curcumin, which has a structure of

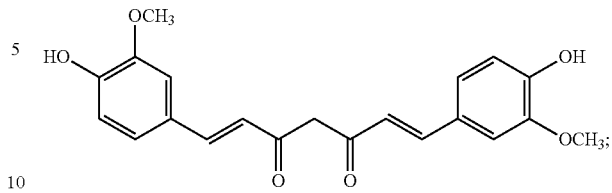

and
(14) artemisetin, which has a structure of

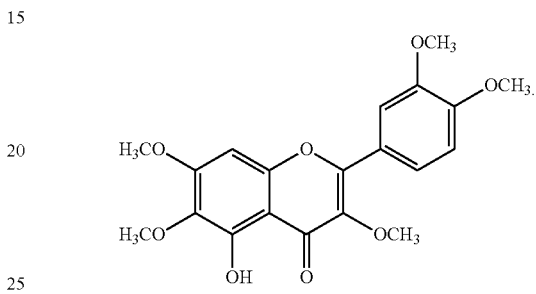

According to some embodiments,
(1) chlorogenic acid is present in the mixture at a level of about 5-10% (e.g., 5, 5.5, 6, 6.5, 7, 7.5, 8, 8.5, 9, 9.5, or 10%) by weight (i.e., 5-10 wt %), based on the total weight of the mixture;
(2) leonurine is present in the mixture at a level of about 0.1-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2%) by weight (i.e., 0.1-2 wt %), based on the total weight of the mixture;
(3) schaftoside is present in the mixture at a level of about 0.1-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2%) by weight (i.e., 0.1-2 wt %), based on the total weight of the mixture;
(4) rutin is present in the mixture at a level of about 5-10% (e.g., 5, 5.5, 6, 6.5, 7, 7.5, 8, 8.5, 9, 9.5, or 10%) by weight (i.e., 5-10 wt %), based on the total weight of the mixture;
(5) isoschaftoside is present in the mixture at a level of about 35-45% (e.g., 35, 35.5, 36, 36.5, 37, 37.5, 38, 38.5, 39, 39.5, 40, 40.5, 41, 41.5, 42, 42.5, 43, 43.5, 44, 44.5, or 45%) by weight (i.e., 35-45 wt %), based on the total weight of the mixture;
(6) isochlorogenic acid is present in the mixture at a level of about 20-30% (e.g., 20, 20.5, 21, 21.5, 22, 22.5, 23, 23.5, 24, 24.5, 25, 25.5, 26, 26.5, 27, 27.5, 28, 28.5, 29, 29.5, or 30%) by weight (i.e., 20-30 wt %), based on the total weight of the mixture;
(7) 4,5-dicaffeoylquinic acid is present in the mixture at a level of about 3-6% (e.g., 3, 3.5, 4, 4.5, 5, 5.5, or 6%) by weight (i.e., 3-6 wt %), based on the total weight of the mixture;
(8) quercetin is present in the mixture at a level of about 0.1-0.5% (e.g., 0.1, 0.2, 0.3, 0.4, or 0.5%) by weight (i.e., 0.1-0.5 wt %), based on the total weight of the mixture;
(9) each of apigenin, glycyrrhizic acid, bisdemethoxycurcumin and demethoxycurcumin is independently present in the mixture at a level of about 1-3% (e.g., 1, 2, or 3%) by weight (i.e., 1-3 wt %), based on the total weight of the mixture;

(10) curcumin is present in the mixture at a level of about 5-10% (e.g., 5, 5.5, 6, 6.5, 7, 7.5, 8, 8.5, 9, 9.5, or 10%) by weight (i.e., 5-10 wt %), based on the total weight of the mixture; and

(11) artemisetin is present in the mixture at a level of about 0.1-0.5% (e.g., 0.1, 0.2, 0.3, 0.4, or 0.5%) by weight (i.e., 0.1-0.5 wt %), based on the total weight of the mixture.

According to some exemplary embodiments, the mixture comprises 7-8 wt % of chlorogenic acid, 0.5-1 wt % of leonurine, 0.5-1.5 wt % of schaftoside, 7-8 wt % of rutin, 38-42 wt % of isoschaftoside, 20-25 wt % of isochlorogenic acid, 4-5 wt % of 4,5-dicaffeoylquinic acid, 0.1-0.3 wt % of quercetin, 1-2 wt % of apigenin, 1-2 wt % of glycyrrhizic acid, 2-3 wt % of bisdemethoxycurcumin, 2-3 wt % of demethoxycurcumin, 5-7 wt % of curcumin, and 0.1-0.3 wt % of artemisetin.

According to one specific example, the mixture comprises 7.7 wt % of chlorogenic acid, 0.8 wt % of leonurine, 1 wt % of schaftoside, 7.2 wt % of rutin, 40.9 wt % of isoschaftoside, 23.8 wt % of isochlorogenic acid, 4.8 wt % of 4,5-dicaffeoylquinic acid, 0.2 wt % of quercetin, 1.2 wt % of apigenin, 1.8 wt % of glycyrrhizic acid, 2.2 wt % of bisdemethoxycurcumin, 2.2 wt % of demethoxycurcumin, 6 wt % of curcumin, and 0.2 wt % of artemisetin.

The pharmaceutical composition of the present disclosure is preferably freeze dried or lyophilized, and stores in a cool and dry environment until use.

Depending on desired purposes, the pharmaceutical composition according to any aspect, embodiment or example of the present disclosure may be formulated with one or more appropriate pharmaceutically acceptable carriers or excipients, and may be formulated into solid, semi-solid, or liquid dosage forms, such as pills, tablets, capsules, powders, pastes, granules, and ointments. As such, the administration of the active ingredients (e.g., the extract of said herbs or herbal parts, or the mixture of said active ingredients) can be achieved in various ways, including oral, buccal, topical, and parenteral etc. administration. In pharmaceutical dosage forms, the pharmaceutical composition of the present disclosure may be administered alone or in combination with other known pharmaceutically active agent to treat muscle atrophy. One of skilled person in the art is familiar with the various dosage forms that are suitable for use in each route. It is to be noted that the most suitable route in any given case would depend on the nature or severity of the disease or condition being treated.

In some embodiments, the pharmaceutical composition of the present disclosure is formulated into a dosage form for parenteral administration, such as topical administration or injection, which includes, but is not limited to, subcutaneous, intramuscular, intraperitoneal and intravenous injection. The pharmaceutical composition may be formulated as isotonic suspensions, solutions or emulsions in oily or aqueous vehicles, and may contain formulatoary agents such as suspending, stabilizing or dispersing agents. Alternatively, the compositions may be provided in dry form such as powders, crystallines or freeze-dried solids with sterile pyrogen-free water or isotonic saline before use. They may be presented in sterile ampoules or vials.

In some embodiments, the pharmaceutical composition of the present disclosure is formulated into solid dosage forms for oral administration. Such solid dosage forms may be capsules, sachets, tablets, pills, lozengens, powders or granules. In such forms, the active ingredients of the present pharmaceutical composition (including chlorogenic acid, leonurine, schaftoside, rutin, isoschaftoside, isochlorogenic acid, 4,5-dicaffeoylquinic acid, quercetin, apigenin, glycyrrhizic acid, bisdemethoxycurcumin, demethoxycurcumin, curcumin, and artemisetin) are optionally mixed with one pharmaceutically acceptable carrier or excipient. Any of the described solid dosage forms may optionally contain coatings and shells, such as enteric coatings, and coatings for modifying the release rate of any of the ingredients. Examples of such coatings are well known in the art. In one example, the pharmaceutical compositions of the present disclosure are tablets such as quick-release tablets. In still another example, the pharmaceutical compositions of the present disclosure are formulated into sustained release forms. In another example, the pharmaceutical compositions of the present disclosure are powders that are encapsulated in soft and hard gelatin capsules.

In some embodiments, the pharmaceutical composition of the present disclosure is formulated into liquid dosage forms for oral administration. The liquid formulation may further include a buffering agent to maintain a desired pH. The liquid dosage formulations may also be filled into soft gelatin capsules. For example, the liquid may include a solution, suspension, emulsion, micro-emulsion, precipitate or any desired liquid media carrying the active ingredients of the present pharmaceutical composition. The liquid may be designed to improve the solubility of the active ingredients of the present pharmaceutical composition to form a drug-containing emulsion or disperse phase upon release. According to one working example of the present disclosure, the active ingredients of the present pharmaceutical composition are formulated with a solvent containing 95% olive oil and 5% glycerol for oral administration.

(ii) Uses of the Present Herbal Compound

The second aspect of the present disclosure pertains to a method of treating muscle atrophy in a subject. The method comprises administering to the subject an effective amount of the pharmaceutical composition in accordance with any aspect, embodiment or example of the present disclosure.

In certain embodiments, the pharmaceutical composition of the present disclosure is given to the subject via topical administration. Alternatively, the pharmaceutical composition of the present disclosure may be given to the subject via oral administration. However, the present disclosure is not limited thereto.

According to some embodiments of the present disclosure, the pharmaceutical composition of the present invention may be orally or topically administered to the subject in a single dose or in multiple doses (e.g., 2, 3, 4, 5, 6, 7, 8, 9, 10, 11, 12, 13, 14, or more doses).

In one embodiment, the subject is a mouse. To elicit a therapeutic effect in mice, about 1-1,000 mg/Kg body weight per dose of the present pharmaceutical composition is administered to the subject; preferably, about 10-100 mg/Kg body weight per dose of the present pharmaceutical composition is administered to the subject; more preferably, 50-70 mg of the present pharmaceutical composition per Kg body weight per dose is sufficient to elicit a therapeutic effect on muscle atrophy in the subject. In one specific example, 60 mg/Kg of the present pharmaceutical composition is administered to the subject thereby achieving the therapeutic effect.

A skilled artisan may readily determine the human equivalent dose (HED) of the present pharmaceutical composition, based on the doses determined from animal studies provided in working examples of this application. Accordingly, the effective amount of the present pharmaceutical composition, suitable for use in a human subject may be in the range of 0.1-100 mg/Kg body weight per dose for human; preferably, 1-10 mg/Kg body weight per dose. In one preferred example, the effective HED is about 4-6 mg/Kg bodyweight per dose.

According to certain preferred embodiments, the pharmaceutical composition of the present disclosure is administered to the subject daily for at least 7 days; for example, being administered to the subject daily for 7, 8, 9, 10, 11, 12, 13, 14, or more day. In one specific example, the pharmaceutical composition of the present disclosure is administered to the subject daily for 14 days.

As could be appreciated, the skilled artisan or clinical practitioner may adjust the dosage or regime in accordance with the physical condition of the patient or the severity of the diseases.

Depending on intended purposes, the present pharmaceutical composition can be applied to the subject, alone or in combination with additional therapies that have some beneficial effects on the prevention or treatment of muscle atrophy. The present pharmaceutical composition can be applied to the subject before, during, or after the administration of the additional therapies.

The subject treatable by the present pharmaceutical composition and/or method is a mammal, for example, human, mouse, rat, guinea pig, hamster, monkey, swine, dog, cat, horse, sheep, goat, cow, and rabbit. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example

Materials and Methods
Preparation of the Present Pharmaceutical Composition (ATG-125)

Seven herbal ingredients, including the leaves of *Artemisia argyi* (512 g), the leaves of mulberry (*Moms alba* L.; 512 g), the leaves of *Leonurus japonicus* Houtt. (512 g), the leaves of *Capsicum annuum* L. (256 g), the leaves of *Lophatherum gracile* Brongn (256 g), the roots of *Curcuma longa* (103 g), and the roots of *Glycyrrhiza uralensis* (103 g), were soaked in 15 L of 95% ethanol at room temperature for 1 day followed by filtration. The filtrate was retained, and the herbal ingredients were subjected to another soaking treatment in the same manner as previously described. The filtrates were combined, and extracted in 70° C. water-bath for 4 hours followed by filtration. The extraction steps were repeated twice. All separate extractions were mixed and concentrated under reduced pressure. The following yields were obtained: 331.11 g (14.69%).

According to the analytic results of high performance liquid chromatography (HPLC) and liquid chromatography-mass spectrometry (LC/MS), the thus-obtained ethanol extract contained chlorogenic acid (0.38% by weight), leonurine (0.04% by weight), schaftoside (0.05% by weight), rutin (0.36% by weight), isoschaftoside (2.03% by weight), isochlorogenic acid (1.18% by weight), 4,5-dicaffeoylquinic acid (0.24% by weight), quercetin (0.01% by weight), apigenin (0.06% by weight), glycyrrhizic acid (0.09% by weight), bisdemethoxycurcumin (0.11% by weight), demethoxycurcumin (0.11% by weight), curcumin (0.3% by weight), and artemisetin (0.01% by weight), based on the total weight of the ethanol extract (data not shown).

Prior to use in in vivo experiments, 1.5 g of the ethanol extract was dissolved in 100 ml solvent consisting of 95% olive oil and 5% glycerol, and the solution was designated as "ATG-125" solution.

Animal Model—Topical Administration

Male C57BL/6J (6 and 18 months) mice were fed standard chow and water ad libitum, and housed under conditions of control temperature (26° C.) and illumination (12-hour light/dark cycle). Mice were randomized into four groups (n=5 per group), including, (1) normal control group: aging mice (age of 18 months) were fed with water for 30 consecutive days (from day 1 to day 30);

(2) sucrose group: aging mice were fed with 30% sucrose (diluted in water) for 30 consecutive days (from day 1 to day 30) to induce muscle atrophy, and further topically administered with 100 μl olive oil (i.e., 100 μl olive oil was topically applied to the abdomen of the mice; serving as the negative control group) once per day from day 17 to day 30;

(3) ATG-125 group: aging mice were fed with 30% sucrose (diluted in water) for 30 consecutive days (from day 1 to day 30), and further topically administered with 60 mg/kg of ATG-125 solution (diluted in olive oil; i.e., 60 mg/kg of ATG-125 solution was topically applied to the abdomen of the mice) once per day from day 17 to day 30; and (4) 4-OHT group: aging mice were fed with 30% sucrose (diluted in water) for 30 consecutive days (from day 1 to day 30), and further intraperitoneally administered with 1 mg/kg of 4-hydroxytamoxifen (4-OHT, diluted in olive oil; serving as the positive control group) once per day from day 17 to day 30.

All animals were sacrificed for further study on day 31. All mice remained on their assigned diets and treatments until they were sacrificed. All protocols were conducted in accordance with the guide for the Care and Use of Laboratory Animals, and were approved by Animal Care and Use Committee.

Animal Model—Oral Administration

Male C57BL/6J (6 and 18 months) mice were fed standard chow and water ad libitum, and housed under conditions of control temperature (26° C.) and illumination (12-hour light/dark cycle). Mice were randomized into four groups (n=5 per group), including:

(1) normal control group: aging mice (age of 18 months) were fed with water for 30 consecutive days (from day 1 to day 30);

(2) sucrose+MPTP group: aging mice were fed with 30% sucrose (diluted in water) for 30 consecutive days (from day 1 to day 30), and further intraperitoneally administered with 15 mg/kg of 1-methyl-4-phenyl-1,2,3,6-tetrahydropyridine (MPTP; dissolved in phosphate buffered saline (PBS) from day 11 to day 17 to induce muscle atrophy; 100 μl olive oil (serving as the negative control group) was orally administered to the aging mice once per day from day 17 to day 30;

(3) sucrose+MPTP+ATG-125 group: aging mice were fed with 30% sucrose (diluted in water) for 30 consecutive days (from day 1 to day 30), and further intraperitoneally administered with 15 mg/kg of MPTP (dissolved in PBS) from day 11 to day 17; 60 mg/kg of ATG-125 solution (diluted in olive oil) was orally administered to the aging mice once per day from day 17 to day 30; and (4) sucrose+MPTP+selegiline group: aging mice were fed with 30% sucrose (diluted in water) for 30 consecutive days (from day 1 to day 30), and further intraperitoneally administered with 15 mg/kg of MPTP (dissolved in PBS) from day 11 to day 17; 1 mg/kg selegiline (diluted in olive oil) was intraperitoneally administered to the aging mice once per day from day 17 to day 30.

All animals were sacrificed for further study on day 31. All mice remained on their assigned diets and treatments until they were sacrificed. All protocols were conducted in accordance with the guide for the Care and Use of Laboratory Animals, and were approved by Animal Care and Use Committee.

Western Blot Analysis

Muscle tissues were harvested immediately from the mice after they were sacrificed, followed by flash frozen in liquid nitrogen and stored at −80° C. Proteins were extracted from muscle tissues with distilled water containing protease inhibitors, and each protein concentration was determined by protein assay kits. Protein (50 μg) was analyzed on a 10% sodium dodecyl sulfate polyacrylamide gel electrophoresis (SDS-PAGE), and transferred to a polyvinylidene difluoride (PVDF) membrane. Immunoblotting was performed with various mouse/rabbit monoclonal or polyclonal antibodies, followed by the incubation of the appropriate secondary antibody coupled with horseradish peroxidase (HRP). The blot was developed with a chemiluminescence system according to the manufacturer's instructions. The optical densities of the bands were quantified using software. Antibodies used in this experiment included, anti-phosphorylated AMP-activated protein kinase (pAMPK) antibody, anti-AMPK antibody, anti-phosphorylated forkhead box O3a (pFOXO3a) antibody, anti-FOXO3a antibody, anti-muscle RING-finger protein-1 (MURF1) antibody, anti-β-actin antibody, anti-sirtuin 1 (SIRT1) antibody, anti-proliferator-activated receptor (PPAR)-γ coactivator-1α (PGC1α) antibody, anti-uncoupling protein 1 (UCP1) antibody, anti-UCP2 antibody, anti-UCP3 antibody, anti-phosphorylated insulin-like growth factor-1 receptor (pIGF1R) antibody, anti-IGF1R antibody, anti-phosphorylated insulin receptor substrate 1 (pIRS1) antibody, anti-IRS1 antibody, anti-phosphorylated phosphoinositide 3-kinase (pPI3K) antibody, anti-PI3K antibody, anti-phosphorylated AKT (pAKT) antibody, anti-AKT antibody, anti-phosphorylated mammalian target of rapamycin (pmTOR) antibody, anti-mTOR antibody, anti-phosphorylated ribosomal S6 kinase (pS6K) antibody, anti-S6K antibody, anti-phosphorylated eukaryotic translation initiation factor 4E (eIF4E)-binding protein 1 (p4EBP1) antibody, and anti-4EBP1 antibody.

Histology, Immunohistochemistry and Immunofluorescence

Muscle tissues of mice were fixed in 4% paraformaldehyde, processed for paraffin embedding and cut into 5 μm thick sections. Before immunostaining, tissue samples were deparaffinized through xylene and graded alcohol series, as in routine processing. The endogenous peroxidase activity was blocked by hydrogen peroxidase treatment. Tissue samples were then washed with distilled water and transferred to Tris-buffered saline plus 0.5% TWEEN® 20, pH 7.4 (TBS-T) containing 5% normal goat serum for 30 minutes. Then, tissue samples were incubated with anti-pAMPK, anti-Glut4, anti-pFOXO3A, anti-FOXO3A, anti-MuRF1, anti-PGC1α, anti-UCP1, anti-UCP2, anti-UCP3, anti-pIGF1R, anti-pIRS1, anti-pPI3K, anti-pAKT, anti-pmTOR, anti-pS6K, anti-p4EBP1, anti-lipofuscin, and MITOTRACKER™ at room temperature for 2 hours. Tissue samples were incubated with the secondary antibody (ALEXAFLUOR® 488, ALEXAFLUOR® 633, anti-mouse or anti-rabbit antibody) at room temperature for 1 hour. All antibodies were diluted in 2% non-immune goat serum in phosphate-buffered saline with TWEEN® (PBST) buffer. Tissue samples were incubated with 3,30-diaminobenzidine (DAB) for 5-10 minutes, and hematoxylin or 4',6-diamidino-2-phenylindole (DAPI) was used for nuclear staining.

RNA Isolation and Real-Time PCR Analysis

Total RNA was isolated from 0.2 g of muscle tissues using RNA extraction kit. For qRT-PCR (real-time reverse transcription-PCR), equal amounts of RNA were retro-transcribed to cDNA using cDNA reverse transcription kit according to the manufacturer's instruction. atrogin-1, klotho, mitochondrial transcription factor A (TFAM), SIRT1, PGC1α, nuclear respiratory factor 1 (NRF1), UCP1, and UCP2 mRNA expressions were evaluated using the SYBR® Green PCR master mix. Relative expression was calculated using the ΔΔCt method with normalization to constitutive genes.

Statistical Analysis

Data were given as mean±standard error of the mean (mean±S.E.M.). Comparisons of the data between groups were calculated using Mann-Whitney's rank sum test and Wilcoxon's sum of rank test. $P<0.05$ was considered statistically significant.

Example 1 Effect of ATG-125 Solution on Muscle Atrophy-Associated Molecules

As described in Materials and Methods, sucrose was used to induce muscle atrophy in aging mice. The sucrose-induced mice were independently treated with specified treatments, including olive oil, ATG-125 solution, and 4-OHT, for 14 days. The expression levels of different muscle atrophy-associated molecules, including pAMPK, AMPK, pFOXO3a, FOXO3a, MuRF1, lipofuscin, atrogin-1 and klotho, in the muscle tissues of mice were examined in this example. The results were respectively depicted in FIGS. 1 to 3.

Figure 2:
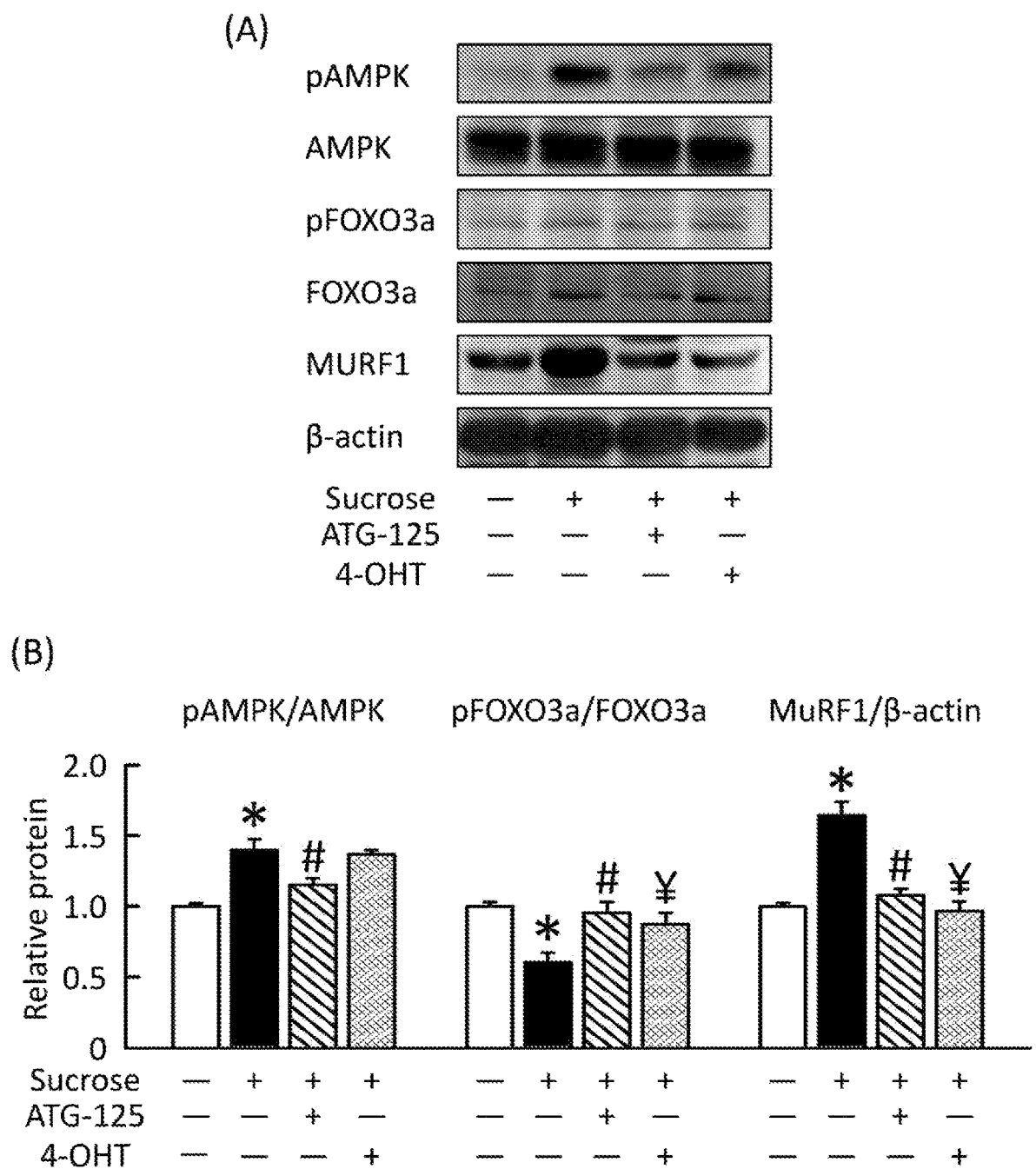
FIG. 2 depicts the effect of the present ATG-125 on protein levels of specified molecules in muscle tissues of mice administered with specified treatments according to Example 1 of the present disclosure; Panel (A): the expression levels of pAMPK, AMPK, pFOXO3a, FOXO3a, MuRF1, and β-actin proteins; Panel (B): the expression ratios of pAMPK to AMPK, pFOXO3a to FOXO3a, and MuRF1 to β-actin; results were expressed as the mean±S.E.M. of five independent experiments, and statistical significance of differences between means was assessed using an unpaired Student's t-test; *$p<0.05$, the normal control group compared to the sucrose group; #$p<0.05$, the sucrose group compared to the sucrose+ATG-125 group; ¥$P<0.05$, the sucrose group compared to the sucrose+4-OHT group.
Figure 3:
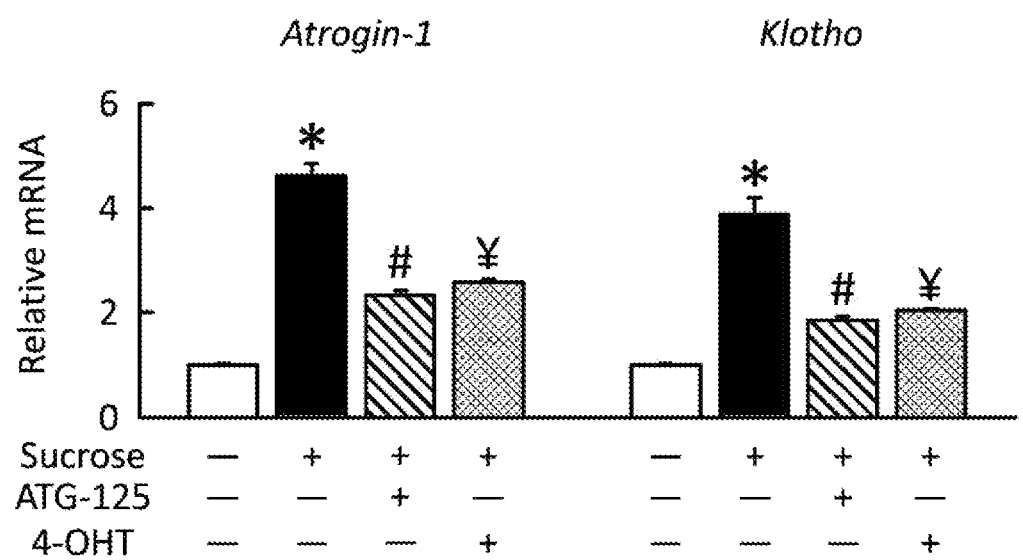
FIG. 3 is a histogram depicting the effect of the present ATG-125 on atrogin-1 and klotho mRNAs in muscle tissues of mice administered with specified treatments according to Example 1 of the present disclosure; results were expressed as the mean±S.E.M. of five independent experiments, and statistical significance of differences between means was assessed using an unpaired Student's t-test; *$p<0.05$, the normal control group compared to the sucrose group; #$p<0.05$, the sucrose group compared to the sucrose+ATG-125 group; ¥$P<0.05$, the sucrose group compared to the sucrose+4-OHT group.

Adipocytes and degenerated myofibers were found in muscle tissues of aging mice fed with sucrose (FIG. 1). Further, compared to the normal control group, the intake of sucrose increased the protein levels of pAMPK, FOXO3a, MuRF1 and lipofuscin (four proteins known to mediate the progression of muscle atrophy; FIGS. 1 and 2), and the mRNA levels of Atrogin-1 and Klotho (the expressions of which are known to induce muscle atrophy; FIG. 3) in the muscle tissues of mice. The treatment of ATG-125 or 4-OHT decreased the levels of adipocytes and degenerated myofibers in muscles, and significantly reversed the adverse effect of sucrose on muscle tissues of aging mice (FIGS. 1 to 3).

These results demonstrated that the present ATG-125 solution may provide a therapeutic effect on muscle atrophy via down-regulating the molecules in AMPK, FOX3, and MuRF1 signaling pathways.

Example 2 Effect of ATG-125 Solution on mTOR/Insulin Signaling Pathway and Muscle Protein Synthesis It is known that insulin signaling impairment (i.e., the elevation of blood sugar levels) leads to muscle atrophy, and signaling activation of mTOR/insulin pathway enhances muscle protein synthesis and positively regulates muscle mass in patients having muscle atrophy. Accordingly, the effect of the present ATG-125 solution on molecules in mTOR/insulin signaling pathway, including IGF1R, IRS1, PI3K, AKT, mTOR, S6K and 4EBP1, was evaluated in this example, and the results were depicted in FIGS. 4A and 4B.

Figure 4A:
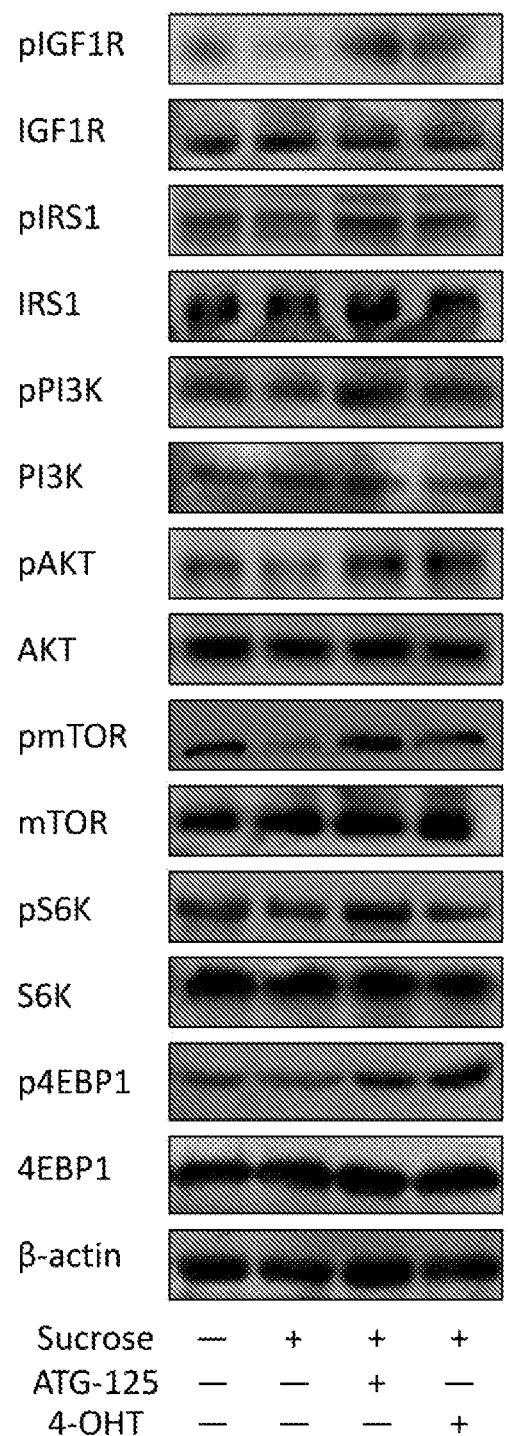
FIGS. 4A and 4B respectively depict the effect of the present ATG-125 on mTOR/insulin signaling pathway in muscle tissues of mice administered with specified treatments according to Example 2 of the present disclosure.
Figure 4B:
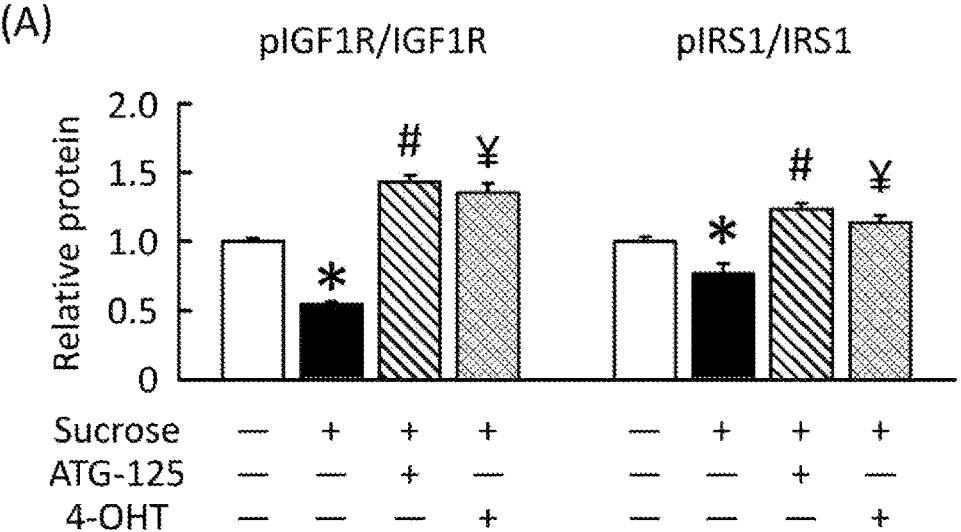
Figure 4B:
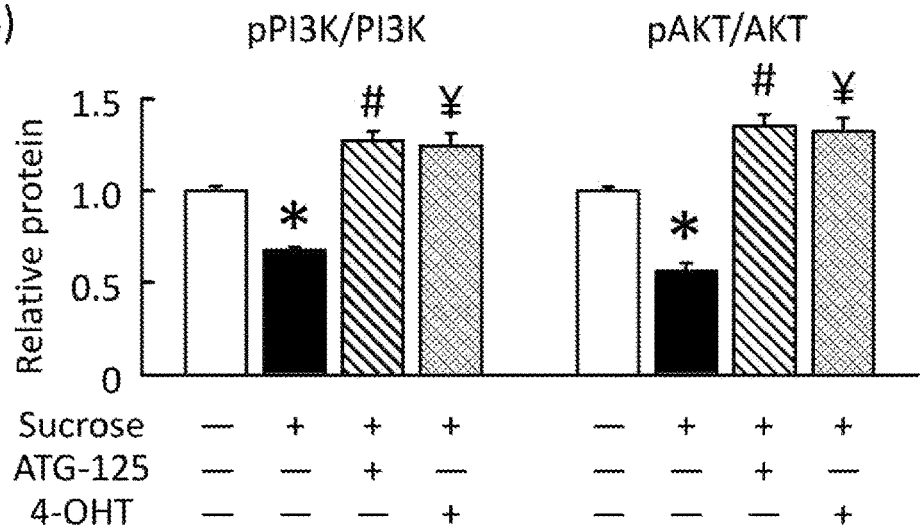
Figure 4B:
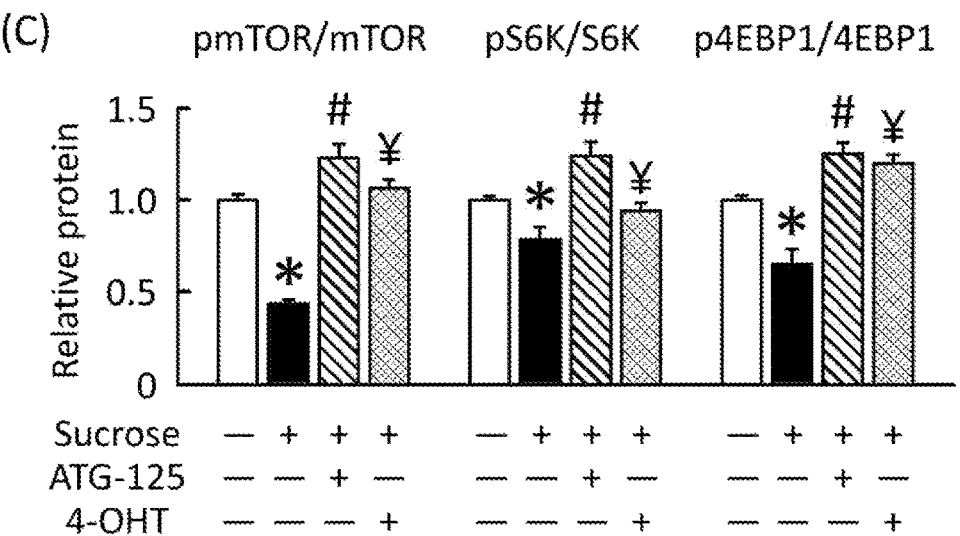

As the data of FIGS. 4A and 4B depicted, the levels of pIGF1R, pIRS1, pPI3K, pAKT, pmTOR, pS6K and p4EBP1 proteins (i.e., the activations of IGF1R, IRS1, PI3K, AKT, mTOR, S6K and 4EBP1) were significantly reduced in aging mice fed with sucrose, while the treatment of ATG-125 or 4-OHT enhanced the phosphorylated levels (i.e., activations) of these mTOR/insulin signaling molecules. Surprisingly, the present ATG-125 solution had a more benefic effect than 4-OHT treatment (FIGS. 4A and 4B).

The data demonstrated that the present ATG-125 solution improved sucrose-induced insulin signaling impairment via up-regulating the mTOR/insulin pathway, and accordingly, enhanced muscle protein synthesis in the sucrose-induced mice.

Example 3 Effect of ATG-125 Solution on Improving Mitochondrial Function

Mitochondria play an essential role in energy production, redox homeostasis, and the regulation of cell death pathways. It has been reported that both morphology and function of mitochondria undergo obvious changes during muscle atrophy. Thus, whether ATG-125 solution improves the mitochondrial function in the animal having muscle atrophy was evaluated in this example, and the results were respectively depicted in FIGS. 5 and 6.

Figure 5:
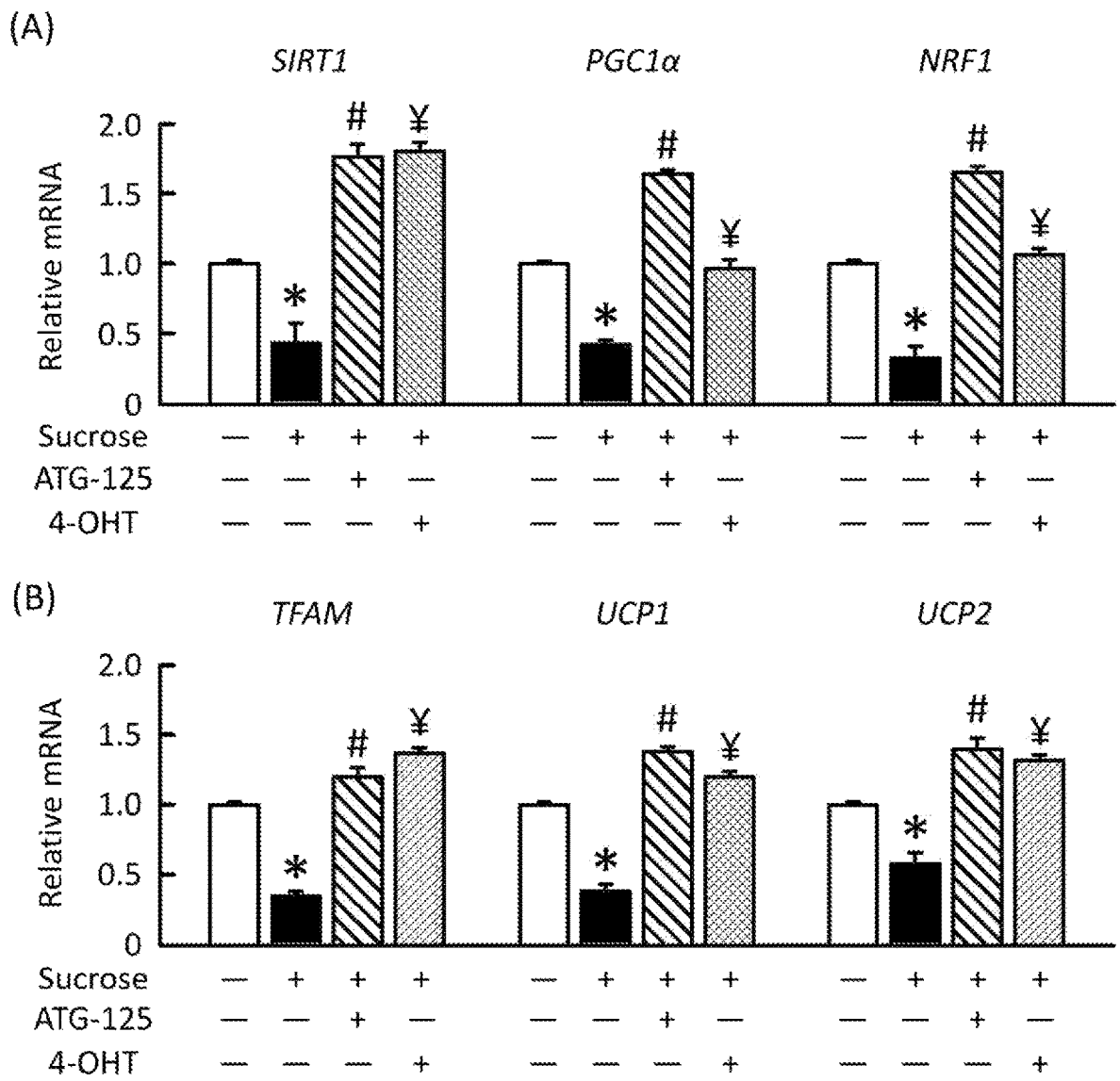
FIG. 5 depicts the effect of the present ATG-125 on specified mitochondrial molecules in muscle tissues of mice administered with specified treatments according to Example 3 of the present disclosure; Panel (A): mRNA levels of sirtuin 1 (SIRT1), proliferator-activated receptor (PPAR)-γ coactivator-1α (PGC1α), and nuclear respiratory factor 1 (NRF1); Panel (B): mRNA levels of mitochondrial transcription factor A (TFAM), uncoupling protein 1 (UCP1) and UCP2; results were expressed as the mean±S.E.M. of five independent experiments, and statistical significance of differences between means was assessed using an unpaired Student's t-test; *$p<0.05$, the normal control group compared to the sucrose group; #$p<0.05$, the sucrose group compared to the sucrose+ATG-125 group; ¥$P<0.05$, the sucrose group compared to the sucrose+4-OHT group.
Figure 6:
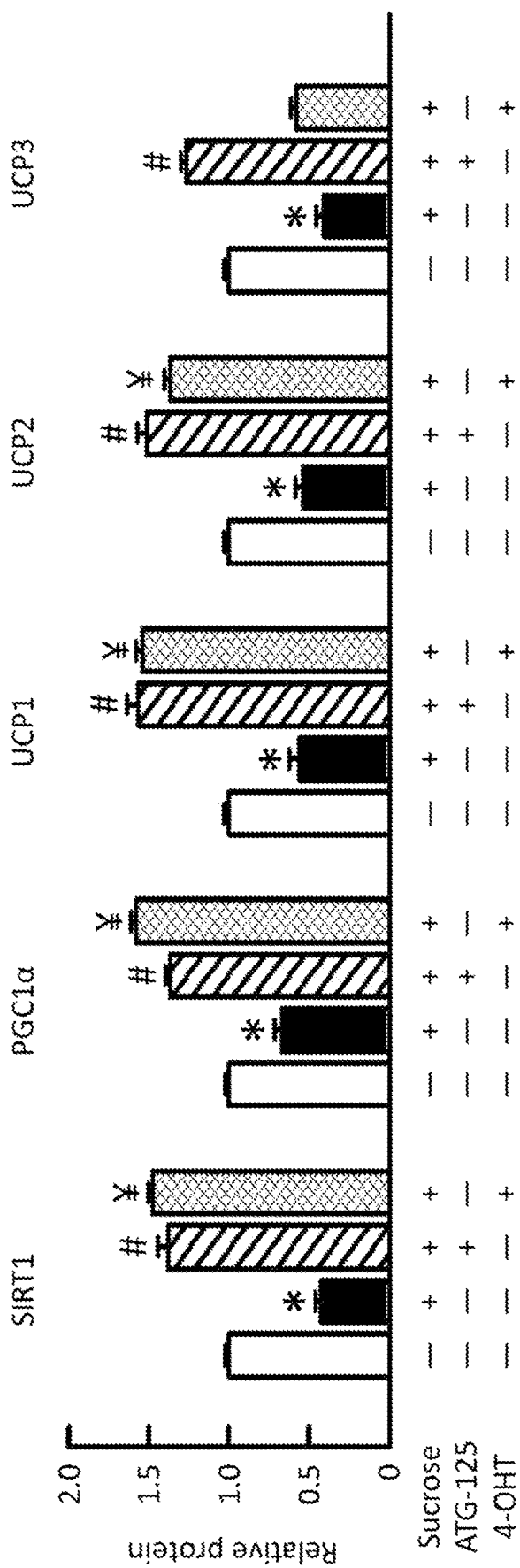
FIG. 6 depicts the effect of the present ATG-125 on protein levels of SIRT1, PGC1α, UCP1, UCP2, and UCP3 in muscle tissues of mice administered with specified treatments according to Example 3 of the present disclosure; results were expressed as the mean±S.E.M. of five independent experiments, and statistical significance of differences between means was assessed using an unpaired Student's t-test; *$p<0.05$, the normal control group compared to the sucrose group; #$p<0.05$, the sucrose group compared to the sucrose+ATG-125 group; ¥$P<0.05$, the sucrose group compared to the sucrose+4-OHT group.

Compared to the normal control group, the intake of sucrose decreased the muscular levels of different mitochondrial molecules, each of which is known to mediate mitochondrial biogenesis and/or function (FIGS. 5 and 6). Specifically, the data of Panels (A) and (B) of FIG. 5 respectively indicated that the intake of sucrose decreased the mRNA levels of SIRT1, PGC1α, NRF1, TFAM, UCP1 and UCP2 in the muscle tissues of mice. The data of FIG. 6 further confirmed that the mice fed with sucrose had decreased protein levels of SIRT1, PGC1α, UCP1, UCP2, UCP3 in their muscle tissues as compared with the mice fed with water. The treatment of ATG-125 or 4-OHT increased the expression levels of these mitochondrial biogenesis mediators in the muscle tissues of the sucrose-induced aging mice (FIGS. 5 and 6). It is noted that compared to 4-OHT, ATG-125 treatment provided a more beneficial effect on the sucrose-induced mice (FIGS. 5 and 6).

Example 4 Effect of ATG-125 Solution on Muscle Atrophy-Associated Molecules

As described in Materials and Methods, sucrose and MPTP were used to induce muscle atrophy in aging mice. The sucrose and MPTP-induced mice were independently treated with specified treatments, including olive oil, ATG-125 solution, and selegiline, for 14 days. The expression levels of different muscle atrophy-associated molecules, including atrogin-1 and klotho, in the muscle tissues of mice were examined in this example. The results were respectively depicted in FIG. 7.

Figure 7:
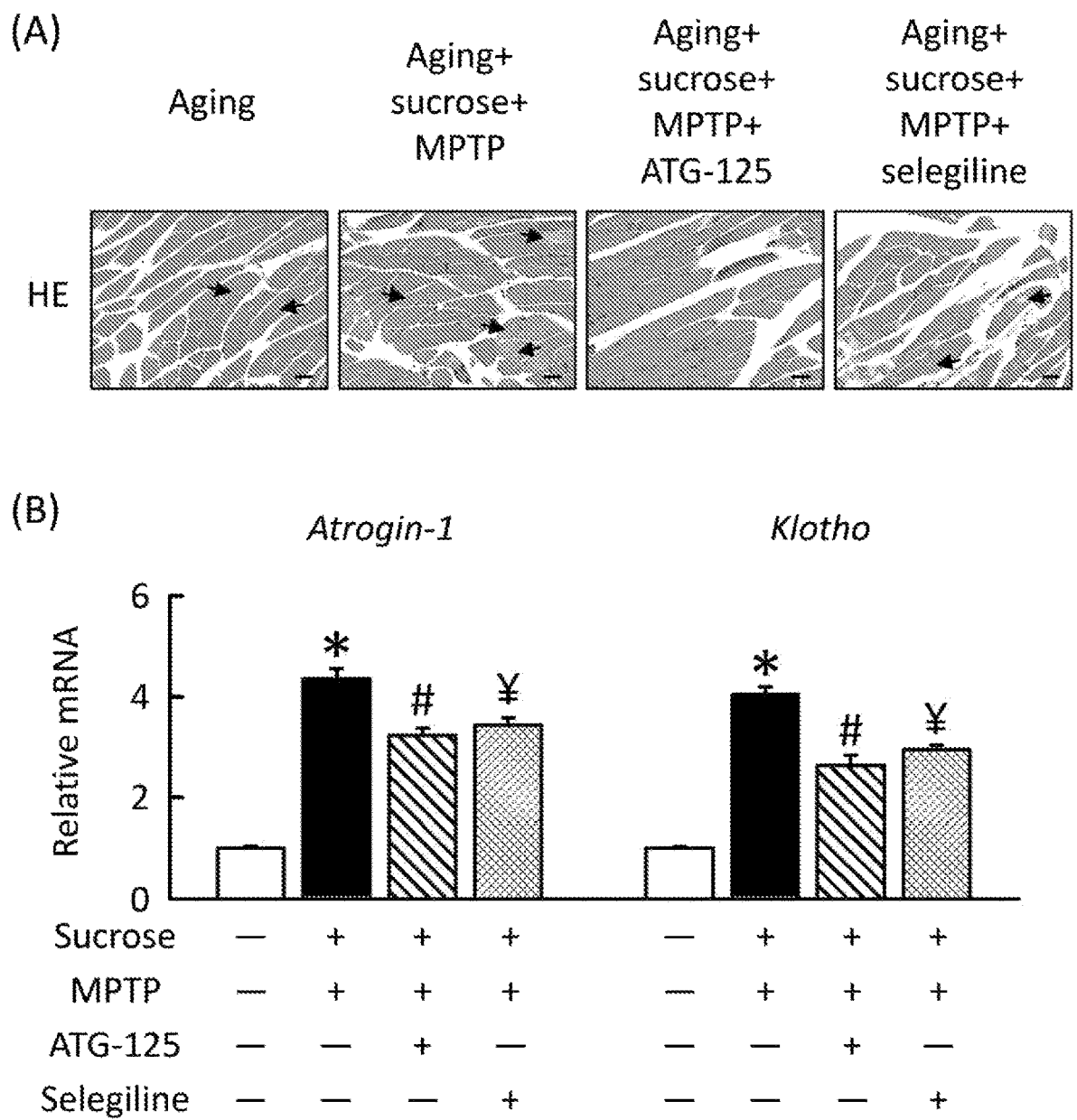
FIG. 7 are representative photographs of the muscle tissues of mice administered with specified treatments according to Example 1 of the present disclosure, Panel (A): the muscle tissues were stained by hematoxylin and eosin (H&E); the positive cells were marked by arrows; scale bar: 100 μm; Panel (B): the histogram depicting the effect of the present ATG-125 on atrogin-1 and klotho mRNAs in muscle tissues of mice administered with specified treatments according to Example 4 of the present disclosure; results were expressed as the mean±S.E.M. of five independent experiments, and statistical significance of differences between means was assessed using an unpaired Student's t-test; *p<0.05, the normal control group compared to the sucrose+MPTP group; #p<0.05, the sucrose+MPTP group compared to the sucrose+MPTP+ATG-125 group; ¥P<0.05, the sucrose group compared to the sucrose+MPTP+selegiline group.

Degenerated myofibers were found in muscle tissues of aging mice fed with sucrose (FIG. 7). Further, compared to the normal control group, the intake of sucrose and MPTP increased the mRNA levels of Atrogin-1 and Klotho (the expressions of which are known to induce muscle atrophy; FIG. 7) in the muscle tissues of mice. The treatment of ATG-125 or selegiline decreased the levels of degenerated myofibers in muscles, and significantly reversed the adverse effect of sucrose and MPTP on muscle tissues of aging mice (FIG. 7).

These results demonstrated that the present ATG-125 solution may provide a therapeutic effect on muscle atrophy via down-regulating the expression of atrogin-1 and klotho.

Example 5 Effect of ATG-125 Solution on Improving Mitochondrial Function

Mitochondria play an essential role in energy production, redox homeostasis, and the regulation of cell death pathways. It has been reported that both morphology and function of mitochondria undergo obvious changes during muscle atrophy. Thus, whether ATG-125 solution improves the mitochondrial function in the animal having muscle atrophy was evaluated in this example, and the results were respectively depicted in FIG. 8.

Figure 8:
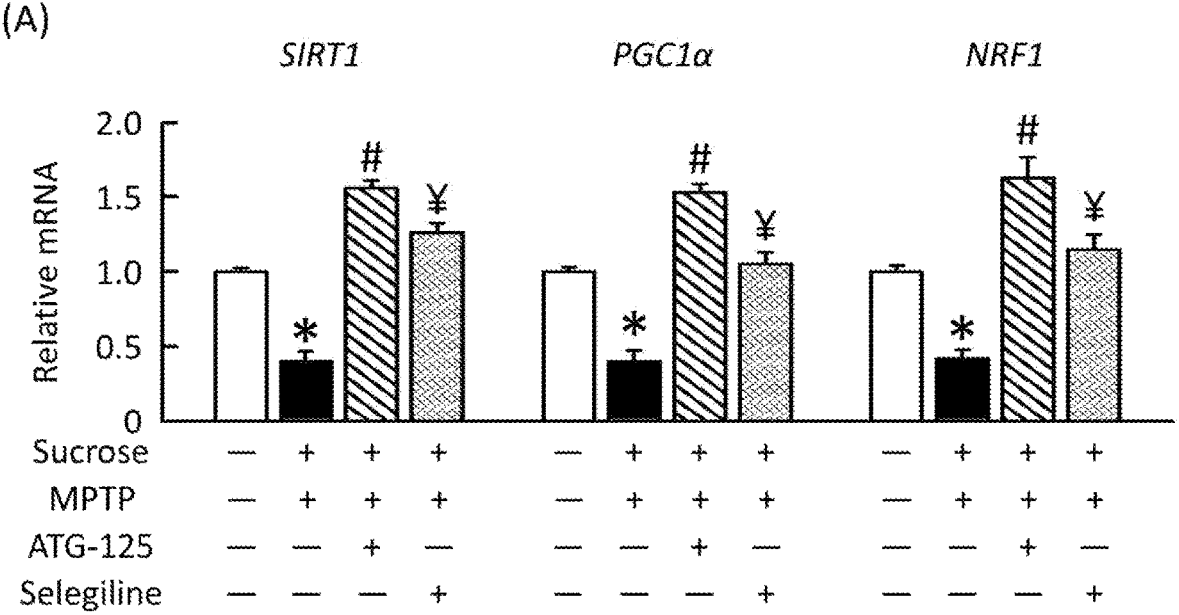
FIG. 8 depicts the effect of the present ATG-125 on specified mitochondrial molecules in muscle tissues of mice administered with specified treatments according to Example 5 of the present disclosure; Panel (A): mRNA levels of sirtuin 1 (SIRT1), proliferator-activated receptor (PPAR)-γ coactivator-1α (PGC1α), and nuclear respiratory factor 1 (NRF1); Panel (B): mRNA levels of mitochondrial transcription factor A (TFAM), uncoupling protein 1 (UCP1) and UCP2; results were expressed as the mean±S.E.M. of five independent experiments, and statistical significance of differences between means was assessed using an unpaired Student's t-test; *p<0.05, the normal control group compared to the sucrose+MPTP group; #p<0.05, the sucrose+MPTP group compared to the sucrose+MPTP+ATG-125 group; ¥P<0.05, the sucrose group compared to the sucrose+MPTP+selegiline group.
Figure 8:
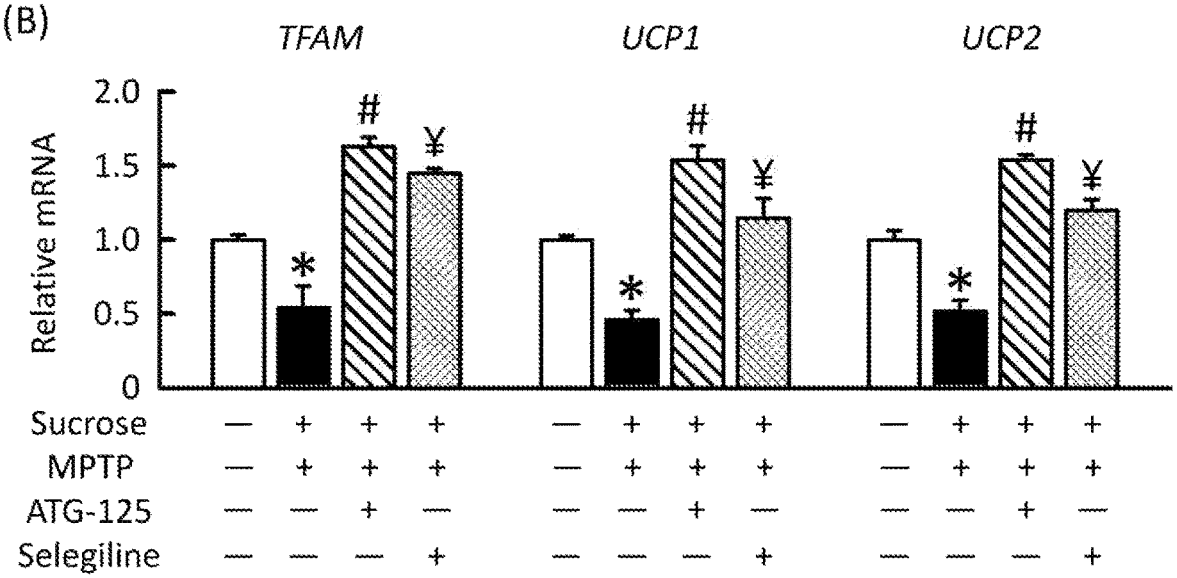

Compared to the normal control group, the intake of sucrose decreased the muscular levels of different mitochondrial molecules, each of which is known to mediate mitochondrial biogenesis and/or function (FIG. 8). Specifically, the data of Panels (A) and (B) of FIG. 8 respectively indicated that the intake of sucrose decreased the mRNA levels of SIRT1, PGC1α, NRF1, TFAM, UCP1 and UCP2 in the muscle tissues of mice. The treatment of ATG-125 or selegiline increased the expression levels of these mitochondrial biogenesis mediators in the muscle tissues of the sucrose and MPTP-induced aging mice (FIG. 8). It is noted that compared to selegiline, ATG-125 treatment provided a more beneficial effect on the sucrose-induced mice (FIG. 8).

These data indicated that the present ATG-125 solution improved mitochondrial function in sucrose and sucrose/MPTP-induced atrophy mice.

In conclusion, the present disclosure provides a pharmaceutical composition (i.e., ATG-125 solution), which provides a potential means to treat muscle atrophy via regulating the expression of different molecules in atrophy pathogenic pathway and enhancing mitochondrial function in atrophy animals. Thus, the present pharmaceutical composition may serve as a therapeutic agent for preventing and/or treating muscle atrophy thereby improving the life span and life quality of patients.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating muscle atrophy in a human in need thereof consisting essentially of administering to the human in need thereof a therapeutically effective amount of an ethanol extract of *Artemisia argyi, Morus alba* L., *Leonurus japonicus* Houit, *Capsicum annuum* L., *Lophatherm gracile* brongn, *Curcuma longa* and *Glycyrrhiza uralensis* to effectively treat the muscle atrophy in the human in need thereof.

2. The method of claim 1, wherein the ethanol extract is orally or topically administered to the human in need thereof.

3. The method of claim 2, wherein the ethanol extract is administered to the human in need thereof daily for at least 7 days.

4. The method of claim 3, wherein the ethanol extract is administered to the human in need thereof daily for 14 days.

5. The method of claim 1, wherein the ethanol extract is 5%-10 wt % of chlorogenic acid, 0.1 wt. %-2 wt % of leonurine, 0.1 wt. %-2 wt % of schaftoside, 5 wt. %-10 wt % of rutin, 35 wt. %-45 wt % of isoschaftoside, 20 wt. %-30 wt % of isochlorogenic acid, 3 wt. %-6 wt % of 4,5-dicaffeoylquinic acid, 0.1 wt. %-0.5 wt % of quercetin, 1 wt. %-3 wt % of apigenin, 1 wt. %-3 wt % of glycyrrhizic acid, 1 wt. %-3 wt % of bisdemethoxycurcumin, 1 wt. %-3 wt % of demethoxycurcumin, 5 wt. %-10 wt % of curcumin, and 0.1 wt. %-0.5 wt % of artemisetin.

6. The method of claim 5, wherein the ethanol extract is 7 wt. %-8 wt % of chlorogenic acid, 0.5 wt. %-1 wt % of leonurine, 0.5 wt. %-1.5 wt % of schaftoside, 7 wt. %-8 wt % of rutin, 38 wt. %-42 wt % of isoschaftoside, 20 wt. %-25 wt % of isochlorogenic acid, 4 wt. %-5 wt % of 4,5-dicaffeoylquinic acid, 0.1 wt. %-0.3 wt % of quercetin, 1 wt. %-2 wt % of apigenin, 1 wt. %-2 wt % of glycyrrhizic acid, 2 wt. %-3 wt % of bisdemethoxycurcumin, 2 wt. %-3 wt % of demethoxycurcumin, 5 wt. %-7 wt % of curcumin, and 0.1 wt. %-0.3 wt % of artemisetin.

7. The method of claim 1, wherein the ethanol extract is produced by extracting the herbal mixture at about 50° C.-80° C. for about 3 hours-5 hours, the herbal mixture consists of the leaves of the *Artemisia argyi*, the leaves of the *Morus alba* L., the leaves of the *Leonurus japonicus* Houtt, the leaves of the *Capsicum annuum* L., the leaves of the *Lophatherum gracile* Brongn, the roots of the *Curcuma longa*, and the roots of the *Glycyrrhiza uralensis* in 95% ethanol.

8. The method of claim 7, wherein the leaves of the *Artemisia argyi*, the leaves of the *Morus alba* L., the leaves of the *Leonurus japonicus* Houtt, the leaves of the *Capsicum annuum* L., the leaves of the *Lophatherum gracile* Brongn, the roots of the *Curcuma longa*, and the roots of the *Glycyrrhiza uralensis* are present in the herbal mixture at a weight ratio of about 4-6:4-6:4-6:2-3:2-3:1:1, respectively.

9. The method of claim 8, wherein the weight ratio is about 5:5:5:2.5:2.5:1:1, respectively.

* * * * *